US00PP16358P3

(12) United States Plant Patent

Iwaki et al.

(10) Patent No.: US PP16,358 P3
(45) Date of Patent: Mar. 21, 2006

(54) *PETUNIA* PLANT NAMED 'SUNPURPLE'

(50) Latin Name: *Petunia hybrida*
Varietal Denomination: Sunpurple

(75) Inventors: Kazunari Iwaki, Omihachiman (JP); Takuro Ishihara, Higashikurume (JP); Kiyoshi Miyazaki, Hikone (JP); Kenichi Suzuki, Ibaraki (JP); Shinya Miyano, Katori-gun (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 75 days.

(21) Appl. No.: 10/789,360

(22) Filed: Feb. 26, 2004

(65) Prior Publication Data

US 2005/0193455 P1 Sep. 1, 2005

(51) Int. Cl.
*A01H 5/00* (2006.01)

(52) U.S. Cl. ..... Plt./356
(58) Field of Classification Search ..... Plt./356
See application file for complete search history.

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP9,322 | P | 10/1995 | Tachibana et al. |

FOREIGN PATENT DOCUMENTS

| | | |
|---|---|---|
| JP | PBR 13924 | 6/2002 |
| JP | PBR 14542 | 9/2002 |

OTHER PUBLICATIONS

"1999–2000 Seed & Plant Catalog" 1999 Ball Horticultural Company, USA.
"Suntory Collection 2004" 2003 Moerheim New Plant bv.

*Primary Examiner*—Kent Bell
(74) *Attorney, Agent, or Firm*—Christie, Parker and Hale, LLP

(57) ABSTRACT

Disclosed herein is a new and distinct variety of *Petunia* plant named 'Sunpurple' having a decumbent growth habit and long stems. 'Sunpurple' has abundant branching, and great profusion of blooms, the whole plant remaining in bloom for a considerable period of time. The flowers are single and medium size, the petals having vivid reddish purple color. The bottom and the outside color of the corolla throat is deep reddish purple. The plant exhibits high resistance to heat, cold, rain and diseases.

2 Drawing Sheets

Botanical classification: *Petunia hybrida*.
Varietal denomination: 'Sunpurple'.

BACKGROUND OF THE VARIETY

The present invention relates to a new and distinct variety of *Petunia* plant, which originated from crossing a seedling of a *Petunia* variety called 'Red Madness' (unpatented) as the female parent and a *Petunia* wild species called '70-200' (unpatented) as the male parent.

The *Petunia* is a very popular plant that is used for flower bedding and potting in the summer season. There are only a few *Petunia* varieties that do not have an upright growth habit and that have a high resistance to rain, heat, and diseases. The *Petunia* plants such as REVOLUTION series, 'Revolution Purple pink' (U.S. Plant Pat. No. 6,915), 'Revolution Brilliant pink' (U.S. Plant Pat. No. 6,914), 'Revolution Brilliantpink-Mini' (U.S. Plant Pat. No. 6,899), and 'Revolution Blue vein' (U.S. Plant Pat. No. 9,322) are decumbent type plants having long stems, a lower plant height, abundant branching, and a high resistance to heat, rain and diseases. However, there are only a few *Petunia* varieties having a decumbent plant shape, a great profusion of flowers, vivid reddish purple petals and a high resistance to rain, heat, and diseases. Accordingly, this invention was aimed at obtaining a new variety having vivid reddish purple petals together with the above features.

The female parent 'Red Madness' used in the crossing to produce 'Sunpurple' is a cultivar having compact and spreading growth habit with medium size single flowers, the petals having a strong red color.

The male parent '70-200' used in the crossing to produce 'Sunpurple' is a strain of wild *Petunia* species having decumbent growth habit with much branching. It has small size single flowers, the petals having vivid reddish purple color.

In April 2000, crossing of 'Red Madness' as the female parent and '70-200' as the pollen parent was conducted at Yokaichi, Shiga, Japan. In August 2000, 80 seedlings were obtained from that crossing. These seedlings were grown in pots in glasshouses and were evaluated. One seedling was selected in view of its growth habit, flower size and color in October 2000. That seedling was propagated by cuttings and a trial was carried out by flower potting and bedding from April to September 2001. The botanical characteristics of that plant were then examined, using similar varieties 'Sunripami' (unpatented) and 'Sunrovein' (U.S. Plant patent application Ser. No. 10/789,408) for comparison. As a result, it was concluded that this *Petunia* plant is distinguishable from any other variety, whose existence is known to us, and uniform and stable in its characteristics. The instant plant reproduces true to type in successive generations of asexual reproduction. The new variety of *Petunia* plant was named 'Sunpurple'.

In the following description, the color-coding is in accordance with the Colour Chart of The Royal Horticultural Society, London, England (R.H.S.).

SUMMARY OF THE VARIETY

This new variety is unlike any *Petunia* commercially available variety known to the inventors, as evidenced by the following unique combinations of characteristics.

1. Decumbent growth habit with long stems.
2. Abundant branching and great profusion of blooms.
3. The flowers are single and medium size. The petal color is vivid reddish purple (near R.H.S. N74A).
4. The plant has a high resistance to cold, heat, rain and diseases.

The new variety 'Sunpurple' differs from the similar variety 'Sunripami' in the following points.

1. The leaf of 'Sunpurple' is longer than that of 'Sunripami'.
2. The leaf of 'Sunpurple' is thinner than that of 'Sunripami'.
3. The flower of 'Sunpurple' is larger than that of 'Sunripami'.
4. The bottom color of the corolla throat of 'Sunpurple' is deep reddish purple (near R.H.S. 72A), while that of 'Sunripami' is moderate purple (near R.H.S. 83B).
5. The outside color of the corolla throat of 'Sunpurple' is deep reddish purple (near R.H.S. N79B), while that of 'Sunripami' is strong purple (near R.H.S. 83D).
6. The apex shape of the petal tip of 'Sunpurple' is obtuse. That of 'Sunripami' is rounded.
7. The flowering time of 'Sunpurple' is later than that of 'Sunripami'.

The new variety 'Sunpurple' differs from the similar variety 'Sunrovein' in the following points.

1. The plant height of 'Sunpurple' is lower than that of 'Sunrovein'.
2. The leaf of 'Sunpurple' is longer than that of 'Sunrovein'.
3. The leaf of 'Sunpurple' is thinner than that of 'Sunrovein'.
4. The petal color of 'Sunpurple' is vivid reddish purple (near R.H.S. N74A), while that of 'Sunrovein' is vivid purplish red (near R.H.S. 71B) with deep purplish red (near R.H.S. 71A) vein.
5. The bottom color of the corolla throat of 'Sunpurple' is deep reddish purple (near R.H.S. 72A), while that of 'Sunrovein' is moderate purplish red (near R.H.S. 64A).
6. The outside color of the corolla throat is deep reddish purple (near R.H.S. N79B), while that of 'Sunrovein' is light purplish pink (near R.H.S. 62C).

BRIEF DESCRIPTION OF THE PHOTOGRAPH

The depicted plants had been produced by the use of cuttings and were photographed during July 2003 at an age of approximately 6 months while growing outdoors in 15 cm pots at Yokaichi-shi, Shiga-ken, Japan, under typical outdoor conditions for that region.

DESCRIPTION OF THE VARIETY

Figure 1:
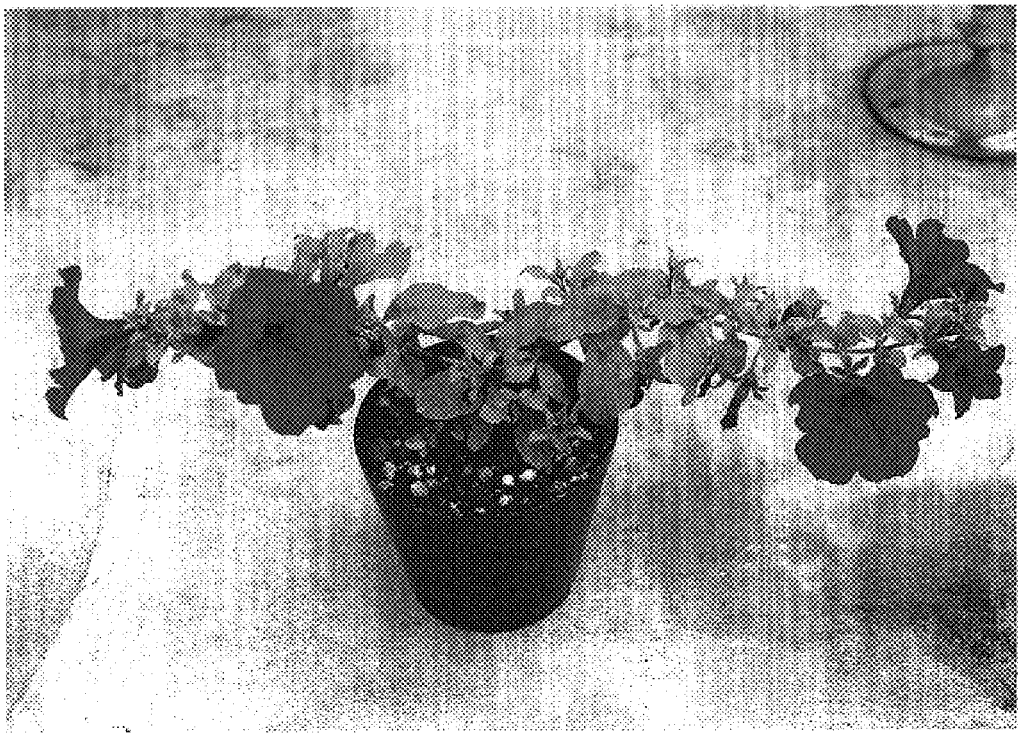
FIG. 1 is a photograph of a typical plant of the new variety of *Petunia* plant 'Sunpurple'.
Figure 2:
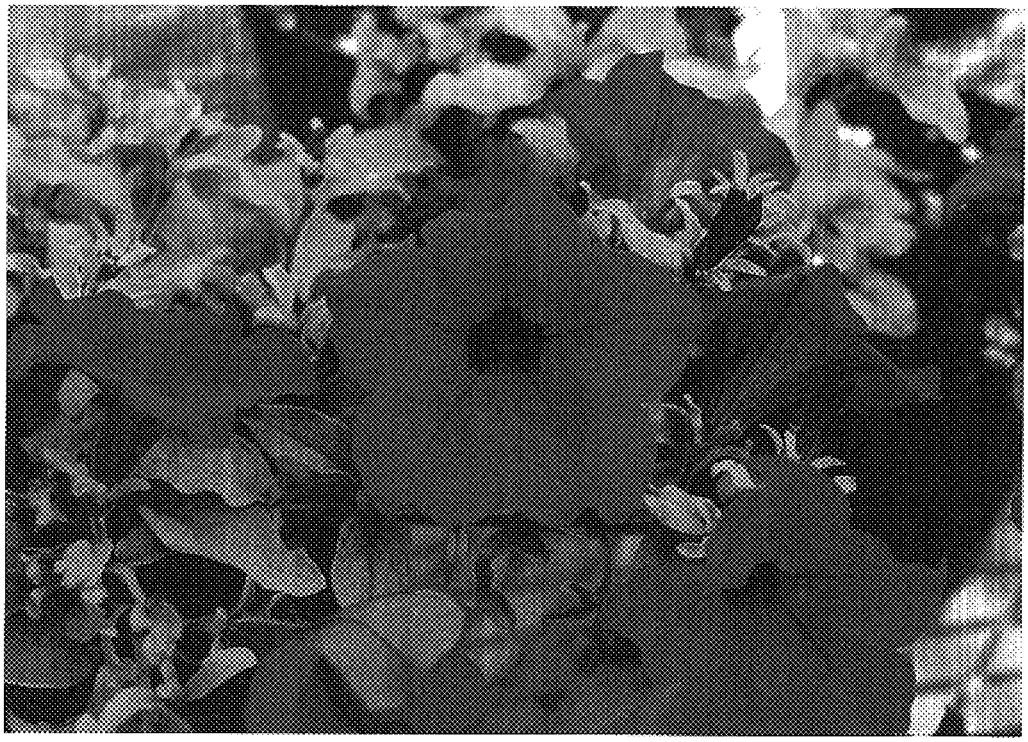
FIG. 2 is a photograph of flowers and leaves of the new variety of *Petunia* plant 'Sunpurple'.

The botanical characteristics of the new and distinct variety of *Petunia* plant named 'Sunpurple' at an age of 4 months, at Yokaichi, Shiga, Japan, are as follows.

Plant:
- *Growth habit.*—Decumbent.
- *Plant height.*—Approximately 12.3 cm.
- *Spreading area of plant.*—Approximately 33.2 cm.
- *Blooming period.*—April to late October in the southern Kanto area, Japan. The plant shape does not change throughout this period. A typical flower commonly lasts approximately 5 days on the plant when experiencing a temperature of approximately 20° C.

Stem:
- *Length.*—Approximately 30 cm.
- *Thickness.*—Approximately 2.5 mm.
- *Pubescence.*—Present and typical for the species.
- *Branching.*—Abundant.
- *Internode length.*—Approximately 2.2 cm.
- *Color.*—Near R.H.S. 144A (strong yellow green).

Leaf:
- *Whole shape.*—Elliptic. The apex shape is acute, and the base shape is attenuate.
- *Margin.*—Entire.
- *Length.*—Approximately 6.4 cm.
- *Width.*—Approximately 3.5 cm.
- *Color.*—Upper side color is near R.H.S. 144A (strong yellow green). Bottom side color is near R.H.S. 146C (moderate olive green).
- *Thickness.*—Approximately 0.2 mm.
- *Pubescence.*—Sparse.

Petiole: (Indistinct).
- *Length.*—Approximately 3.0 mm.
- *Diameter.*—Approximately 1.0 mm.
- *Color.*—Near R.H.S. 144B.

Buds:
- *Shape.*—Cylindrical.
- *Length.*—Approximately 4.5 cm.
- *Diameter.*—Approximately 7.0 mm.
- *Color.*—Toward apex, Near R.H.S. N77B; base, near R.H.S. N79B; venation, near R.H.S. N92A.

Flower:
- *Facing direction.*—Slanted upward.
- *Type.*—Single.
- *Shape.*—Funnel-shape, with five-fissured limb.
- *Diameter.*—Approximately 7.4 cm.
- *Depth.*—Approximately 5.8 cm.
- *Throat diameter.*—Distal end, approximately 1.5 cm.
- *Tube diameter.*—Proximal end, approximately 4.0 mm.

Petals:
- *Whole shape.*—Very broadly obtrullate.
- *Apex shape.*—Obtuse.
- *Width.*—Approximately 4.0 cm.
- *Length (from the throat).*—Approximately 3.5 cm.
- *Margin.*—Entire, undulated.
- *Color.*—Upper side of the petal, near R.H.S. N74A; underside of the petal, near R.H.S. N78A with near N92A venation.
- *Upper color of the corolla throat.*—Near R.H.S. N90B with N92A venation.
- *Bottom color of the corolla throat.*—Near R.H.S. 72A.
- *Outside color of corolla tube.*—Near R.H.S. N79B.
- *Reproductive organs.*—1 normal pistil and 5 normal stamens. Color of pistil is near R.H.S. 150C (light yellow green). Color of stamen is near R.H.S. 157C (light yellow green).

*Peduncle*.—Approximately 1.3 mm in diameter and approximately 1.9 cm in length. Color — Near R.H.S. 144B. Surface — Pubescent.

*Calyx*.—Medium. 5 sepals fused at the base.

Sepals:

*Shape*.—Narrow elliptic.

*Apex shape*.—Rounded.

*Base*.—Fused.

*Margin*.—Entire, undulated.

*Surface*.—Pubescent.

*Length*.—Approximately 2.5 cm.

*Width*.—Approximately 6.0 mm.

*Color*.—Upper surface, near R.H.S. 144A; lower surface, toward apex, near R.H.S. 144A; base, near R.H.S. N77A.

*Physiological and ecological characteristics*.—High resistance to cold, heat, rain and diseases. Moderate resistance to pests.

This new variety of *Petunia* plant is most suitable for flower bedding and potting, particularly in hanging pots or planters, and is excellent for use as ground cover. Pinching of old blossoms will enhance the formation of new blossoms.

We claim:

1. A new and distinct variety of *Petunia* plant named 'Sunpurple', substantially as herein illustrated and described.

* * * * *